(12) United States Patent
Lynch et al.

(10) Patent No.: US 8,603,034 B2
(45) Date of Patent: Dec. 10, 2013

(54) ONE PIECE SEALING RESERVOIR FOR AN INSULIN INFUSION PUMP

(75) Inventors: George R. Lynch, Coppell, TX (US); Allen E. Brandenburg, Dripping Springs, TX (US); Bret Price, San Antonio, TX (US)

(73) Assignee: Applied Diabetes Research, Inc., Carrollton, TX (US)

( * ) Notice: Subject to any disclaimer, the term of this patent is extended or adjusted under 35 U.S.C. 154(b) by 1599 days.

(21) Appl. No.: 11/231,737

(22) Filed: Sep. 21, 2005

(65) Prior Publication Data

US 2007/0078393 A1  Apr. 5, 2007

Related U.S. Application Data

(60) Provisional application No. 60/698,323, filed on Jul. 12, 2005.

(51) Int. Cl.
*A61M 37/00* (2006.01)
*A61M 1/00* (2006.01)

(52) U.S. Cl.
USPC .......................... 604/155; 604/151; 604/131

(58) Field of Classification Search
USPC ................................. 604/155, 154
See application file for complete search history.

(56) References Cited

U.S. PATENT DOCUMENTS

| | | | |
|---|---|---|---|
| 3,547,119 A | 12/1970 | Niles et al. | |
| 3,701,345 A | 10/1972 | Hellman et al. | |
| 3,739,778 A | 6/1973 | Monestere, Jr. et al. | |
| 3,996,923 A | 12/1976 | Guerra | |
| 4,106,491 A | 8/1978 | Guerra | |
| 4,126,133 A | 11/1978 | Schwartz | |
| 4,258,940 A | 3/1981 | Fudge | |
| 4,311,136 A | 1/1982 | Weiki et al. | |
| 4,311,137 A | 1/1982 | Gerard | |
| 4,418,944 A | 12/1983 | Haines et al. | |
| 4,430,081 A | 2/1984 | Timmermans | |

(Continued)

FOREIGN PATENT DOCUMENTS

FR  2578746 A1  9/1986

OTHER PUBLICATIONS

American National Standard ANSI/HIMA MD70.1-1983, Dimensional Requirements for Luer Lock Fittings, Figure 7, p. 12.

(Continued)

*Primary Examiner* — Nicholas Lucchesi
*Assistant Examiner* — Weng Lee
(74) *Attorney, Agent, or Firm* — Jackson Walker, LLP

(57) ABSTRACT

A novel one-piece fluid reservoir assembly for use in conjunction with an insulin infusion pump. The single piece fluid reservoir assembly includes a barrel body, a male luer fitting integral with the barrel body, a sealing surface integral with the barrel body, the sealing surface for sealing against the pump housing when the fluid reservoir assembly is inserted into the pump housing. Further, the barrel includes, as part of the one-piece fluid reservoir assembly, threads for engagement with threads on an opening in the fluid pump so that the fluid assembly can be inserted into the fluid pump, engage the threads and rotation therewith will locate the fluid reservoir assembly within the pump. Thereafter, a piston in the pump may be incrementally advanced to act upon a plunger in the barrel assembly to force a fluid within the barrel assembly through the male luer fitting and through a conduit engaged therewith to a remote infusion set.

12 Claims, 5 Drawing Sheets

(56) References Cited

U.S. PATENT DOCUMENTS

| | | | |
|---|---|---|---|
| 4,531,937 A | 7/1985 | Yates | |
| 4,645,495 A | 2/1987 | Vaillancourt | |
| 4,755,173 A | 7/1988 | Konopka et al. | |
| 4,936,833 A | 6/1990 | Sams | |
| 5,019,054 A | 5/1991 | Clement et al. | |
| 5,098,394 A | 3/1992 | Luther | |
| 5,176,662 A | 1/1993 | Bartholomew et al. | |
| 5,201,717 A | 4/1993 | Wyatt et al. | |
| 5,242,411 A | 9/1993 | Yamamoto | |
| 5,257,980 A | 11/1993 | Van Antwerp et al. | |
| 5,281,206 A | 1/1994 | Lopez | |
| 5,300,045 A | 4/1994 | Plassche, Jr. | |
| 5,330,450 A | 7/1994 | Lopez | |
| 5,427,145 A | 6/1995 | Grabenkort | |
| 5,545,143 A | 8/1996 | Fischell | |
| 5,545,152 A | 8/1996 | Funderburk et al. | |
| 5,613,663 A | 3/1997 | Schmidt et al. | |
| 5,814,020 A | 9/1998 | Gross | |
| 5,848,990 A | 12/1998 | Cirelli et al. | |
| 5,851,197 A | 12/1998 | Marano et al. | |
| D404,482 S | 1/1999 | Falk et al. | |
| 5,858,001 A | 1/1999 | Tsais et al. | |
| 5,919,167 A * | 7/1999 | Mulhauser et al. | 604/131 |
| 5,968,011 A | 10/1999 | Larsen et al. | |
| 5,980,506 A | 11/1999 | Mathiasen | |
| 6,017,328 A | 1/2000 | Fischell et al. | |
| 6,056,718 A | 5/2000 | Funderburk et al. | |
| 6,093,172 A | 7/2000 | Funderburk et al. | |
| 6,095,997 A | 8/2000 | French et al. | |
| 6,186,982 B1 | 2/2001 | Gross et al. | |
| 6,213,973 B1 | 4/2001 | Eliasen et al. | |
| 6,248,093 B1 * | 6/2001 | Moberg | 604/131 |
| 6,302,866 B1 | 10/2001 | Marggi | |
| 6,355,021 B1 | 3/2002 | Nielsen et al. | |
| 6,419,699 B1 | 7/2002 | Schuessler | |
| 6,423,035 B1 * | 7/2002 | Das et al. | 604/155 |
| 6,482,186 B1 | 11/2002 | Douglas et al. | |
| D471,272 S | 3/2003 | Douglas et al. | |
| D472,316 S | 3/2003 | Douglas et al. | |
| D472,630 S | 4/2003 | Douglas et al. | |
| 6,585,695 B1 * | 7/2003 | Adair et al. | 604/183 |
| 6,629,949 B1 | 10/2003 | Douglas | |
| 6,641,566 B2 | 11/2003 | Douglas et al. | |
| 6,659,982 B2 | 12/2003 | Douglas et al. | |
| 6,673,440 B2 | 1/2004 | Douglas et al. | |
| 6,685,674 B2 | 2/2004 | Douglas et al. | |
| D488,230 S | 4/2004 | Ignotz et al. | |
| 6,752,787 B1 | 6/2004 | Causey, III et al. | |
| 6,800,071 B1 | 10/2004 | McConnell et al. | |
| 6,817,990 B2 | 11/2004 | Yap et al. | |
| 6,854,620 B2 * | 2/2005 | Ramey | 222/63 |
| 6,923,791 B2 | 8/2005 | Douglas | |
| 7,056,302 B2 | 6/2006 | Douglas | |
| 7,063,684 B2 | 6/2006 | Moberg | |
| 7,083,597 B2 | 8/2006 | Lynch et al. | |
| 7,211,068 B2 | 5/2007 | Douglas | |
| 2002/0045867 A1 | 4/2002 | Nielsen et al. | |
| 2002/0123724 A1 | 9/2002 | Douglas et al. | |
| 2002/0173748 A1 | 11/2002 | McConnell et al. | |
| 2003/0125672 A1 | 7/2003 | Adair et al. | |
| 2003/0163090 A1 * | 8/2003 | Blomquist et al. | 604/154 |
| 2004/0003493 A1 | 1/2004 | Adair et al. | |
| 2004/0085215 A1 | 5/2004 | Moberg et al. | |
| 2004/0092873 A1 | 5/2004 | Mobert | |
| 2005/0021000 A1 | 1/2005 | Adair et al. | |
| 2006/0129095 A1 * | 6/2006 | Pinchuk | 604/102.01 |

OTHER PUBLICATIONS

Medtronic MiniMed Paradigm Reservoir, 3 ml, Ref MMT-332A, User Guide.
ISO 594-2:1998(E), 3.2.2 Semi-rigid materials, Figures 1 and 2.
PCT International Search Report of Apr. 3, 2008 and Written Opinion (Applied Diabetes Research, Applicant).

* cited by examiner

ONE PIECE SEALING RESERVOIR FOR AN INSULIN INFUSION PUMP

This application claims priority from, and incorporates herein by reference, U.S. Provisional Patent Application No. 60/698,323, filed Jul. 12, 2005.

FIELD OF THE INVENTION

Fluid reservoirs for use in conjunction with insulin pumps, namely, one-piece fluid reservoirs that include a male luer fitting and can seal to a housing of the insulin pump

BACKGROUND

Infusion pumps are provided for diabetic patients to allow for the infusion into the body of the patient of a regulated amount of insulin or other medication. Existing pumps provide a piston for acting on a fluid reservoir and for urging fluid, such as insulin, from the reservoir through a conduit to an infusion set and into a patient.

Some of the existing infusion pumps, such as that illustrated in U.S. Pat. No. 6,248,093 (incorporated herein by reference), have an O-ring or other means for providing waterproof or water resistant sealing between the fluid reservoir, insertable into the pump, and the pump housing. By providing a waterproof or water resistant engagement between an insertable fluid reservoir and the housing, the pump user may engage in activities, such as showering or other behavior that will subject the pump to water. It can be appreciated that the pump and reservoir combination would, advantageously, be water resistant.

Currently, fluid reservoirs that are used with water resistant pumps have a septum sealed reservoir or a luer nosed reservoir. A reservoir having a septum requires engagement with a piercing member to pierce the septum and provide fluid to a conduit for delivery to an infusion pump. The current reservoirs having a male luer fitting integral therewith, require a separate piece, engageable to the fluid reservoir for adapting the fluid reservoir to the water resistant pump. Thus, both of the current types described need a separate piece, either with or without a piercing member, to adapt the fluid reservoir in water sealing relation to the pump housing. While there are some advantages to this arrangement, Applicants have found advantages in providing in a single piece, integral unit, a fluid reservoir with a male luer fitting at a removed end thereof, which one-piece reservoir is adapted to fit in water sealing relation to an opening in a pump housing.

It is more convenient for a consumer to use with a single piece rather than having to engage one piece (an adaptor) to another (a fluid reservoir) and then the combined assembly to a pump housing. Further, there are some advantages in the manufacturing process for providing a single piece of Applicants' novel design. Further, advantages result from Applicants' use of a single piece design, combined with a luer fitting, which luer fitting can be adapted to receive a needle for removing fluid from a larger insulin container, which same luer fitting may subsequently, after the reservoir is engaged with the pump, accept a common female lure fitting attached to a conduit having an insulin set at the removed end thereof.

Applicants provide a novel one-piece fluid reservoir for engagement with an infusion pump, which one-piece fluid reservoir will achieve, in a single unitary piece, a number of functions. Some of these functions, achieved in a one-piece fluid reservoir engageable with an infusion pump, and the associated structure include the following:

SUMMARY OF THE INVENTION

These and other objects are provided in a fluid reservoir assembly for engaging a fluid pump, the pump having a housing, a fluid reservoir chamber, a threaded, cylindrical reservoir housing chamber opening, and a piston to act on the fluid reservoir assembly when the fluid reservoir is in the reservoir chamber, the fluid reservoir assembly comprising a one-piece barrel assembly, the one-piece barrel assembly including a cylindrical barrel portion having a barrel diameter and having a first open end and a second end, a male luer fitting integral with the second end of the barrel portion, the male luer fitting having an opening at a removed end thereof, the one piece barrel assembly including a neck portion integral with the barrel portion, the neck portion including threads dimensioned to engage the threads of the reservoir housing chamber opening, the one piece barrel assembly including a cylindrical sealing surface dimensioned to lay adjacent the reservoir housing chamber opening of the pump housing in fluid sealing relation, the cylindrical sealing surface integral with the neck, and a plunger dimensioned for slideable receipt into the open end of the one-piece barrel assembly.

1. Thread segments to engage the female threads in the housing or case of the infusion pump to hold the fluid reservoir in place;
2. A sealing surface to seal to the O-ring in the case of the infusion pump to help seal out water;
3. Detents to releasably and lockingly engage recesses in the case of the infusion pump to prevent accidental unscrewing of the fluid reservoir;
4. Vent port(s) to permit pressure in the housing or case of the infusion pump to adjust to the external atmosphere;
5. A small orifice opening in the luer end of the reservoir to allow flow of medication from the reservoir while providing adequate resistance to flow so that the pump can sense, the flow of medication and measure the quantity of medication delivered;
6. Tabs to assist in holding the reservoir while screwing it into the pump; and
7. A plunger and rod with threads adapted to prevent the rod from becoming stuck in the plunger and thus difficult to remove after filling the reservoir.

The one-piece sealing reservoir typically provides a 1.8 ml, 3.0 ml or other capacity reservoir intended for use in a portable infusion pump used for delivery of medication, such as insulin. The fluid reservoir provides a common male luer connection which allows the patient using the infusion pump to connect it to their choice of infusion delivery devices that have a female luer receptacle.

DETAILED DESCRIPTION OF THE PREFERRED EMBODIMENTS

Figure 1:
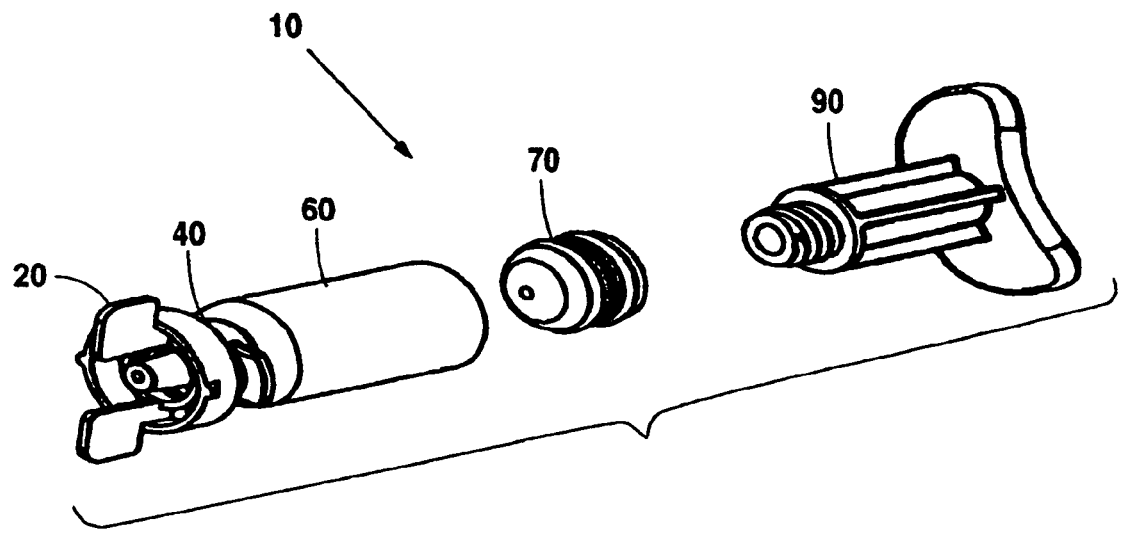
FIG. 1 illustrates an exploded view of applicants' novel one-piece fluid reservoir assembly which may also contain a plunger engagement rod, in perspective view.

FIG. 1 shows a fluid reservoir assembly 10 with a luer portion 20, a neck portion 40, and a barrel portion 60. A plunger 70 slideably engages the inner surface of the barrel portion, and a plunger engagement rod 90 removably engages the plunger. The barrel portion 60 holds the medication to be delivered and receives the plunger, which will mate with a drive piston from the infusion pump (see FIG. 9).

Figure 2:
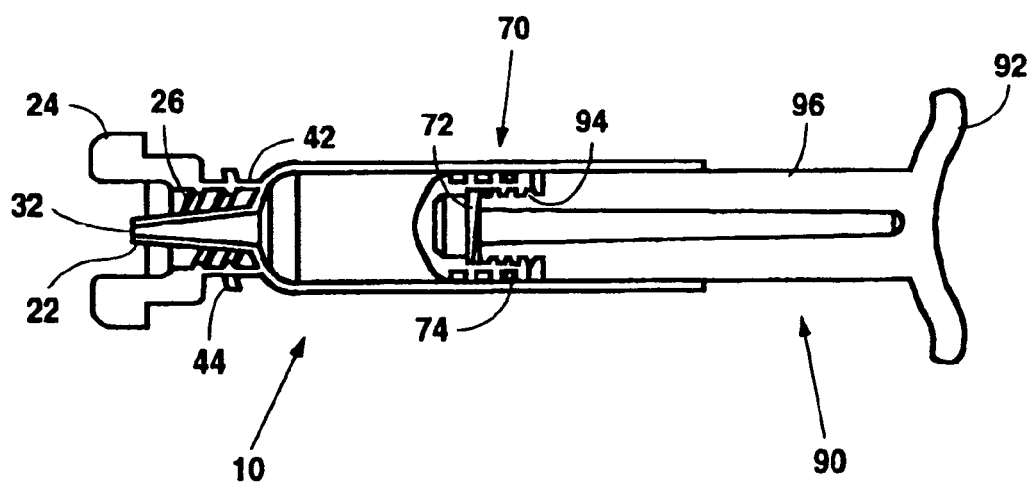
FIG. 2 illustrates applicants' novel fluid reservoir, including the fluid reservoir assembly with the plunger rod engaging the plunger thereof, in cross-section elevational view.

FIG. 2 shows the assembled reservoir 10, plunger 70 and rod 90 in cross section. The plunger 70 has a plunger threaded area 72 to engage with a rod thread area 94 of the rod 90. The plunger typically is adapted to receive one or more O-rings 74 on an outer surface thereof to slideably seal to the barrel portion 60 of the reservoir assembly 10.

Figure 8:
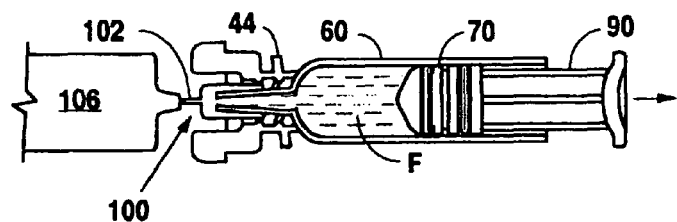
FIG. 8 illustrates the manner in which applicants' fluid assembly may be used to fill an empty fluid reservoir for insertion into the fluid pump.

During filling of the reservoir 10 illustrated in FIG. 8, a handle 92 of the rod 90 in used to draw the plunger 70 back and suck medication from a larger, typically septum sealed, container 106 into the barrel area 60. After filling the reservoir 10, the rod 90 is unscrewed from the plunger 70 and discarded.

Figure 3:
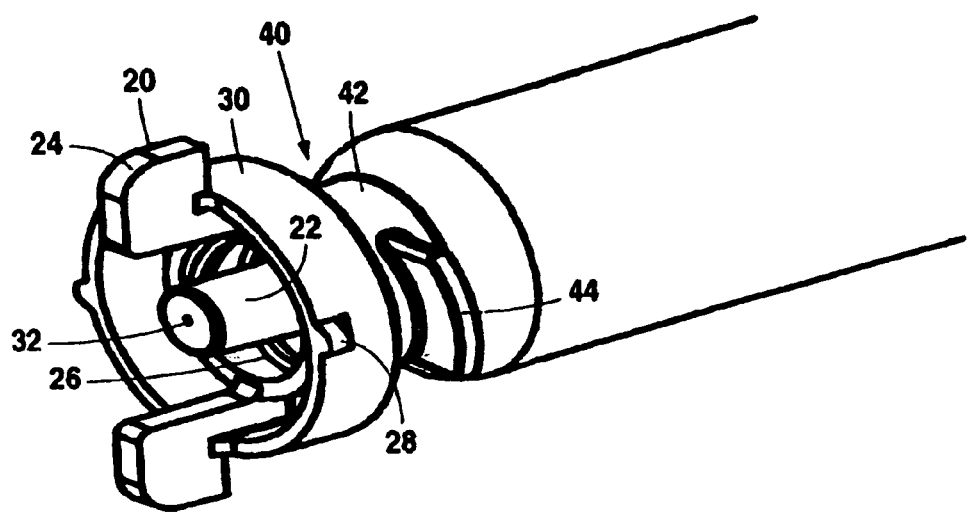
FIG. 3 illustrates a close-up detail view, in perspective, of the second end of the barrel portion showing the integral neck sealing surface, tabs, threads and other related structure, including the male luer fitting in fluid engagement with the interior of the barrel.

FIG. 3 shows details of the luer area 20 and neck area 40. The luer area 20 consists of a standard male luer 22, and optionally threads 26 to receive a threaded female luer receptacle from an infusion delivery set. The standard male luer and associated structure (threads, etc.) may be dimensioned according to ISO594-1 and 594-2 (incorporated herein by reference), provided, however, the opening dimensions as set forth below.

The filled reservoir 10 is inserted, axially, into the infusion pump, barrel end first after removal of the rod 90. When the reservoir 10 is fully inserted into the infusion pump, the thread segments 44 located on the neck 42 engage threads in the infusion pump. Optionally, tabs 24 are provided to facilitate the tightening and loosening of the reservoir in the infusion pump. Sealing surface 30 is dimensioned slightly less than the reservoir chamber opening assembly to seal the reservoir 10 to an O-ring (or O-rings) or other functional equivalents located in the infusion pump housing opening (see FIG. 9). The sealing of the reservoir to the case housing of the infusion pump provides a watertight or water resistant infusion pump/reservoir assembly permitting the patient to wear the infusion pump during swimming, showering or other activities which might otherwise cause water to enter the case and damage the electronic components. Detents 28 may engage recesses in the infusion pump case to prevent accidental unscrewing of the reservoir from the infusion pump. Detents 28 may be integral with the walls of sealing surface 30.

Existing infusion pumps have a means of measuring the volume of medication flowing from the fluid reservoir by determining motion of the drive piston. They sometimes use a sensor located in the drive piston assembly to detect the movement of the plunger in the reservoir. For the sensor to detect the movement of the drive piston, there must be resistance to the flow of medication and hence to the movement of the plunger. Luer 22 has a novel orifice opening 32 which allows medication to flow from the reservoir while providing resistance to the flow. The size of the orifice opening 32 is novel as being very small, from 0.003" to 0.020" (preferred range 0.005-0.010") in diameter. This small diameter of the orifice opening 32 provides a restriction to flow sufficient for the infusion pump to measure the quantity of medication delivered.

Figure 4:
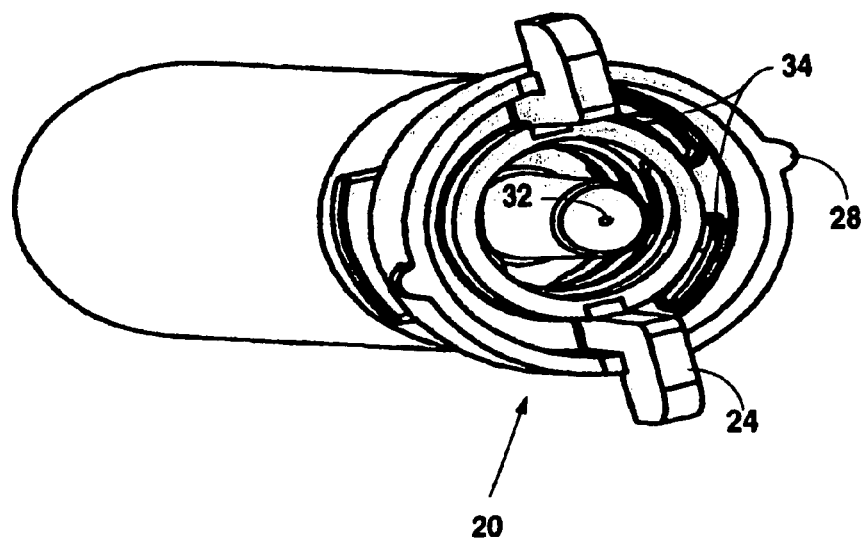
FIG. 4 is a similar perspective view of the assembly of FIG. 3, taken from a different angle.

FIG. 4 is a view of the luer area 20 showing at least one vent port 34.

Figure 5:
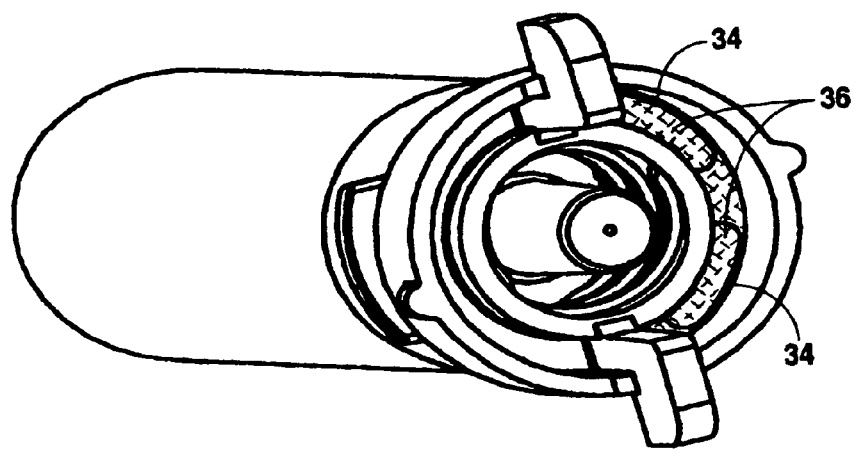
FIG. 5 is a perspective view from the front of applicants' barrel portion of the fluid reservoir assembly showing the vent ports integral therewith and the filter medium bonded or sealed to the external walls of the ports.

FIG. 5 shows a filter medium 36, typically hydrophobic, bonded into the vent port 34. While the infusion pump/reservoir assembly is sealed to prevent water from entering the interior of the case, there should be structure provided to let the internal pressure in the case adjust to the external atmosphere. If the internal pressure in the infusion pump is different from the external atmosphere, the accuracy of medication dosing may be effected. To allow the internal pressure of the infusion pump to adjust to the external atmosphere, vent ports 34 are provided in luer area 20 of reservoir 10. Vent ports 34 are covered typically by a hydrophobic filter material 36. Hydrophobic material permits gas to pass through the material while resisting the passage of water or other liquids, thus permitting water resistant venting. The hydrophobic material may be welded to the reservoir by ultrasonic or heat staking or it may be bonded by other means.

Figure 6:
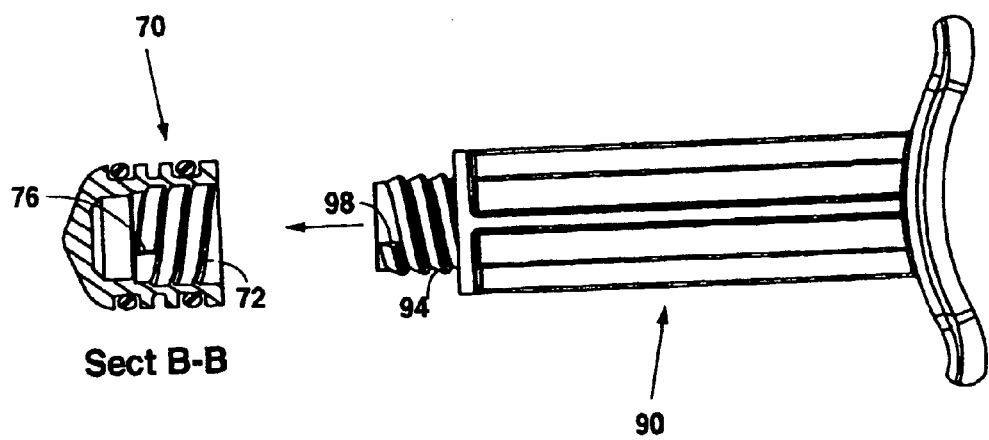
FIG. 6 shows the plunger with an internal threaded area and the rod with the threaded area for threadable engagement with the plunger, illustrating the novel flat ends of the threads in cross-sectional view.

FIG. 6 shows thread area 72 of plunger 70 and thread area 94 of rod 90. The threads 72 of the plunger 70 end in a flat end 76. The threads 94 of the rod 90 also end in a similarly dimensioned flat end 98. When the rod 90 is screwed into the plunger 70, the flat ends 76 and 98 butt against each other before threads 72 and 94 can tighten against one another. Stopping the threads in this manner prevents the rod 90 from becoming stuck in the plunger 70 and difficult to remove after filling the reservoir 10.

Figure 7:
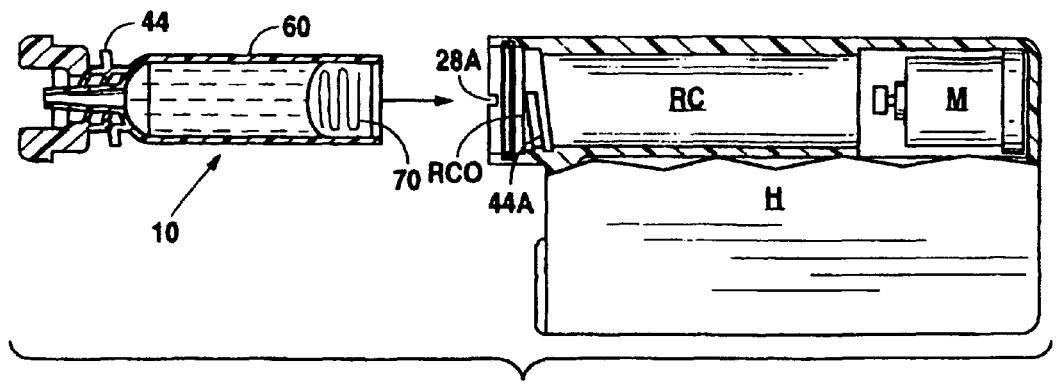
FIG. 7 is a cross-sectional elevational view, partially cut away, showing the manner in which applicants' fluid reservoir assembly engages a housing of a pump having the reservoir chamber and a reservoir chamber opening.

FIG. 7 shows an exploded view of applicants' novel fluid reservoir 10, after the rod has been removed therefrom and after it has been filled, as it engages the housing H of a pump.

Housing H is seen to include a reservoir chamber RC and a reservoir chamber opening RCO. The reservoir chamber opening has detent openings 28A on the walls thereof for receipt of applicants' detents 28. Threads 44, typically in the neck area of the fluid reservoir, are provided to engage threads 44A on the reservoir chamber opening so as to position the fluid-filled fluid assembly 10 within the reservoir chamber. A motor M can drive a drive piston DP axially along the longitudinal axis of the barrel portion 60 so as to engage the piston and drive fluid out of the luer fitting and into a conduit 110 as set forth in FIG. 10.

FIG. 8 illustrates the use of applicant's fluid reservoir assembly to engage a needle assembly 100, which needle assembly has engaged therewith in fluid sealing relation a needle 102. Needle 102 has a removed end with a small orifice in it and is hollow. Needle assembly 100 typically includes a female luer fitting 104, which female luer fitting is designed to and dimensioned to be received snugly in fluid sealing relation to male luer portion 20 of barrel portion of reservoir 10.

Figure 9:
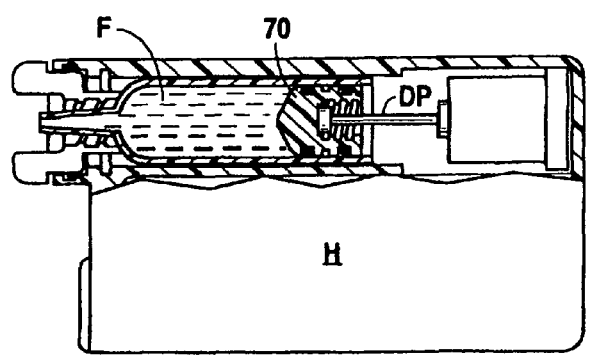
FIG. 9 illustrates in a top elevational view, partially cut away, the manner in which applicants' fluid reservoir assembly engages the reservoir chamber of the housing of the pump.

With the fluid reservoir 10 having needle assembly 100 engaged therewith and, with plunger engagement rod 90 engaged with plunger 70, and plunger 70 in a full forward position against the walls defining the end of the luer barrel portion 60 (which contains male luer portion 20), user can insert needle 102 through a septum of a fluid (typically insulin) container 106. Retraction of plunger engagement rod 90 in the direction indicated in FIG. 8 will allow fluid to be withdrawn from container 106 into fluid reservoir 10. When plunger 70 is at or near the removed open end of barrel portion 60, plunger engagement rod 90 can be rotated and removed from the plunger. Because of applicant's novel flat-end-to-flat-end threaded engagement between plunger engagement rod 90 and plunger 70, plunger 70 should not rotate in the barrel and thus will make rotational disengagement of plunger from the rod easy. With plunger engagement rod 90 discarded, reservoir 10 can be asserted axially into cylindrical pump as illustrated in FIGS. 7 and 9.

Applicant's novel reservoir has a barrel portion, typically of a diameter sufficient to pass through reservoir chamber opening and into the reservoir chamber, aligning with the walls of the chamber so as to present a barrel assembly longitudinal axis aligned with the longitudinal axis of the drive piston. When applicant's reservoir 10 is inserted into housing H, such as a Mini-Med Model MMT-511, threads 44A will engage threads 44 of reservoir 10, and upon engagement and continued rotation of reservoir 10, the reservoir will be drawn into reservoir chamber RC a distance to place sealing surface 30 adjacent O-rings or other sealing means at reservoir chamber opening RCO. Moreover, applicant's detents 28 on the walls of sealing surface 30, typically small projections, may engage cutouts 28A in the walls of reservoir chamber opening RCO as illustrated in FIG. 7.

Figure 10:
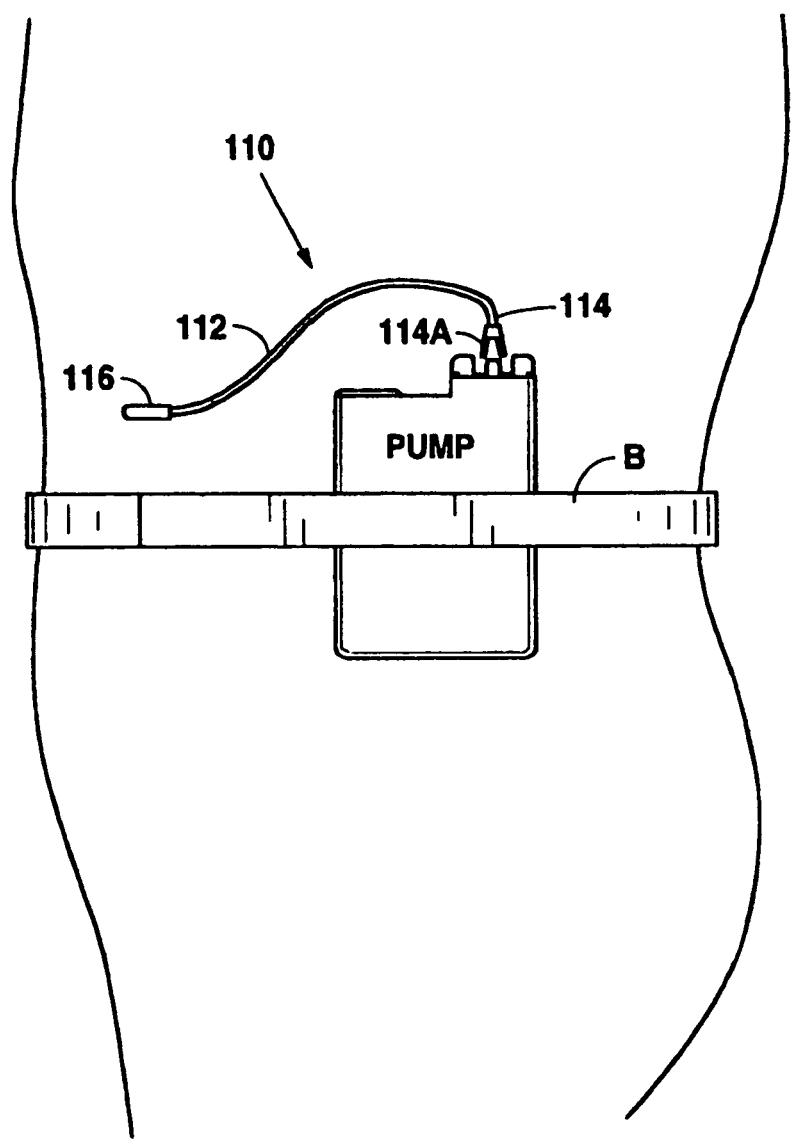
FIG. 10 illustrates in a side elevational view, applicants' novel pump/infusion set assembly wherein the fluid reservoir engages the pump and an infusion set having a conduit with a female luer fitting at the end thereof to engage the male luer fitting of the fluid reservoir.

FIG. 10 shows pump P held in place by a belt B on a user. Pump P shows an infusion set assembly 110 having a fluid conduit 112 engaged therewith. At a near end of the fluid conduit 112 is a female luer fitting 114 for snugly engaging applicant's fluid reservoir 10. A female luer assembly 114 may have threads 114A at a base thereof for threaded engagement with luer threads 26 of fluid reservoir 10. Fluid from the fluid reservoir 10 will be urged, by incremental advances of drive piston DP, through the male and female luer fittings and conduit 112 to an infusion set 116 for infusion into the body of the user in ways known in the trade.

Although the invention has been described with reference to specific embodiments, this description is not meant to be construed in a limited sense. Various modifications of the disclosed embodiments, as well as alternative embodiments of the inventions, will become apparent to persons skilled in the art upon the reference to the description of the invention. It is, therefore, contemplated that the appended claims will cover such modifications that fall within the scope of the invention.

The invention claimed is:

1. A fluid reservoir assembly for engaging a pump, the pump having a housing, a reservoir chamber, a threaded, cylindrical reservoir housing chamber opening having a sealing member, and a piston to act on the fluid reservoir assembly when the fluid reservoir assembly is in the reservoir chamber, the fluid reservoir assembly comprising:
   a one-piece barrel, the one-piece barrel including a cylindrical barrel portion having a barrel diameter and having a first open end and a second end, a male luer fitting integral with the second end of the barrel portion, the male luer fitting having an opening at a removed end thereof, the one piece barrel including a neck portion integral with the barrel portion, the neck portion including integral threads dimensioned to engage the threads of the reservoir housing chamber opening, the one piece barrel including a cylindrical sealing surface radially outward of the neck portion threads and configured to lay adjacent the interior of the reservoir housing chamber opening of the pump housing and engage the sealing member, the cylindrical sealing surface integral with the neck;
   a plunger dimensioned for slideable receipt into the open end of the one-piece barrel;
   wherein the one-piece barrel further includes walls, the walls defining a port, the port dimensioned and located on the one-piece barrel such that the interior of said housing is vented when said fluid reservoir assembly is engaged therewith and said cylindrical sealing surface is laying adjacent in fluid sealing relation to the housing chamber opening in airtight engagement;
   wherein the port is substantially covered with a filter medium capable of filtering water from a gas and allowing the passage of the gas therethrough; and
   further comprising a wall extending from an external surface of the port and substantially surrounding the port, wherein the port is covered with the filter medium adjacent the external surface.

2. The fluid reservoir assembly of claim 1, further comprising a locking assembly for releasably securing the cylindrical barrel portion in the housing.

3. The fluid reservoir assembly of claim 2, wherein the locking assembly includes detents on the walls of the cylindrical sealing surface for engaging walls defining the reservoir housing chamber opening.

4. The fluid reservoir assembly of claim 1, wherein the plunger includes a threaded interior portion and further including a rod having a handle, the rod with a threaded portion, the threaded portion of the rod engageable with the threaded interior portion of the plunger.

5. The fluid reservoir assembly of claim 4, wherein the threads of the plunger include a flat removed end and the threads of the rod include a similarly dimensioned flat removed end adapted to be received flush against the flat removed end of the plunger threads.

6. The fluid reservoir assembly of claim 1, wherein the opening of the removed end of the luer fitting is between 0.003 and 0.020 inches in diameter.

7. The fluid reservoir assembly of claim 1, wherein the diameter of the barrel portion is less than the diameter of the threaded, cylindrical reservoir housing chamber opening.

8. The fluid reservoir assembly of claim 1, wherein the cylindrical sealing surface of the one-piece barrel is dimensioned to contact an "O" ring on the cylindrical reservoir chamber opening.

9. A fluid reservoir assembly for engaging a pump, the pump having a housing, a reservoir chamber, a threaded, cylindrical reservoir housing chamber opening with a sealing member, and a piston to act on the fluid reservoir assembly when the fluid reservoir is in the reservoir chamber, the fluid reservoir assembly comprising:
   a one-piece barrel, the one-piece barrel including:
   a cylindrical barrel portion having a barrel diameter and having a first open end and a second end, a male luer fitting integral with the second end of the barrel portion, the male luer fitting having an opening at a removed end thereof, the one piece barrel including:
a neck portion integral with the barrel portion, the neck portion including threads dimensioned to engage the threads of the reservoir housing chamber opening, the one piece barrel including:
a cylindrical sealing surface radially outward of the neck portion threads and configured to lay adjacent the interior of the reservoir housing chamber opening of the pump housing and engage the sealing member, the cylindrical sealing surface integral with the neck, wherein the one-piece barrel further includes:
a plunger dimensioned for slideable receipt into the open end of the one-piece barrel, the plunger including a threaded interior portion, the plunger adapted to receive "O" rings;
a locking assembly wherein the locking assembly includes detents on the walls of the cylindrical sealing surface for engaging walls defining the reservoir housing chamber opening;
a rod having a handle, the rod with a threaded portion, the threaded portion of the rod engageable with the threaded interior portion of the plunger;
walls defining a port, the port dimensioned and located on the one-piece barrel such that the interior of said housing is vented when said fluid reservoir assembly is engaged therewith and said cylindrical sealing surface is laying adjacent in fluid sealing relation to the housing chamber opening in airtight engagement, wherein the port is substantially covered with a filter medium capable of filter water from a gas and allowing the passage of the gas therethrough, wherein the filter medium is hydrophobic, wherein the opening of the removed end of the luer fitting is between 0.003 and 0.020 inches in diameter, wherein the cylindrical sealing surface of the one-piece barrel is dimensioned to contact an "O" ring on the cylindrical reservoir chamber opening; and
further comprising a wall extending from an external surface of the port and substantially surrounding the port, wherein the port is covered with the filter medium adjacent the external surface.

10. A kit for providing insulin to a patient through an infusion set engaged with the patient, the kit comprising:
a container having insulin therein, the container including a sealing septum;
a needle assembly having a female luer fitting and a needle dimensioned to puncture the sealing septum of the container; and
a pump having a reservoir chamber and a reservoir chamber opening, the reservoir chamber opening with a sealing member therein;
a one-piece barrel, the one-piece barrel including a cylindrical barrel portion having a barrel diameter and having a first open end and a second end, a male luer dimensioned to receive the female luer fitting of the needle assembly and fitting integral with the second end of the barrel portion, the male luer fitting having an opening at a removed end thereof, the one piece barrel including a neck portion integral with the barrel portion, the neck portion including integral threads dimensioned to engage the threads of the reservoir housing chamber opening, the one piece barrel including a cylindrical sealing surface radially outward of the neck portion threads and configured to lay adjacent the interior of the reservoir housing chamber opening of the pump housing and engage the sealing member, the cylindrical sealing surface integral with the neck;
a plunger dimensioned for slideable receipt into the open end of the one-piece barrel;
wherein the one-piece barrel further includes walls, the walls defining a port, the port dimensioned and located on the one-piece barrel such that the interior of said housing is vented when said fluid reservoir assembly is engaged therewith and said cylindrical sealing surface is laying adjacent in fluid sealing relation to the housing chamber opening in airtight engagement;
wherein the port is substantially covered with a filter medium capable of filtering water from a gas and allowing the passage of the gas therethrough; and
further comprising a wall extending from an external surface of the port and substantially surrounding the port, wherein the port is covered with the filter medium adjacent the external surface.

11. An assembly for the delivery of insulin to a diabetic patient, the assembly comprising:
a pump, the pump having a reservoir chamber, a drive piston, and a threaded reservoir chamber opening with a sealing member;
a one-piece barrel, the one-piece barrel including a cylindrical barrel portion having a barrel diameter and having a first open end and a second end, a male luer fitting integral with the second end of the barrel portion, the male luer fitting having an opening at a removed end thereof, the one piece barrel including a neck portion integral with the barrel portion, the neck portion including integral threads dimensioned to engage the threads of the reservoir housing chamber opening, the one piece barrel including a cylindrical sealing surface radially outward of the neck portion threads and configured to lay adjacent the interior of the reservoir housing chamber opening of the pump housing and engage the sealing member, the cylindrical sealing surface integral with the neck;
a plunger dimensioned for slideable receipt into the open end of the one-piece barrel;
wherein the one-piece barrel further includes walls, the walls defining a port, the port dimensioned and located on the one-piece barrel such that the interior of said housing is vented when said fluid reservoir assembly is engaged therewith and said cylindrical sealing surface is laying adjacent in fluid sealing relation to the housing chamber opening in airtight engagement;
wherein the port is substantially covered with a filter medium capable of filtering water from a gas and allowing the passage of the gas therethrough; and
further comprising a wall extending from an external surface of the port and substantially surrounding the port, wherein the port is covered with the filter medium adjacent the external surface.

12. A fluid delivery system, the system comprising:
a pump including a housing, a reservoir chamber, a threaded, cylindrical reservoir housing chamber opening having a sealing member, and a piston to act on a one piece barrel when the one piece barrel is in the reservoir chamber;
the one-piece barrel including a cylindrical barrel portion having a barrel diameter and having a first open end and a second end, a male luer fitting integral with the second end of the barrel portion, the male luer fitting having an opening at a removed end thereof, the one piece barrel including a neck portion integral with the barrel portion, the neck portion including integral threads dimensioned to engage the threads of the reservoir housing chamber opening, the one piece barrel including a cylindrical sealing surface configured to lay adjacent the interior reservoir housing chamber opening of the pump housing and engaging the sealing member, the cylindrical sealing surface integral with the neck; and a plunger dimensioned for slideable receipt into the open end of the one-piece barrel;

wherein the one-piece barrel further includes walls, the walls defining a port, the port dimensioned and located on the one-piece barrel such that the interior of said housing is vented when said fluid reservoir assembly is engaged therewith and said cylindrical sealing surface is laying adjacent in fluid sealing relation to the housing chamber opening in airtight engagement;

wherein the port is substantially covered with a filter medium capable of filtering water from a gas and allowing the passage of the gas therethrough; and further comprising a wall extending from an external surface of the port and substantially surrounding the port, wherein the port is covered with the filter medium adjacent the external surface.

\* \* \* \* \*